(12) United States Patent
King

(10) Patent No.: US 8,825,175 B2
(45) Date of Patent: *Sep. 2, 2014

(54) IMPEDANCE-BASED STIMULATION ADJUSTMENT

(75) Inventor: Gary W. King, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/348,943

(22) Filed: Jan. 12, 2012

(65) Prior Publication Data

US 2012/0109254 A1    May 3, 2012

Related U.S. Application Data

(63) Continuation of application No. 11/414,534, filed on Apr. 28, 2006, now Pat. No. 8,108,049.

(60) Provisional application No. 60/676,609, filed on Apr. 30, 2005.

(51) Int. Cl.
    *A61N 1/18* (2006.01)

(52) U.S. Cl.
    USPC ................. 607/62; 607/28; 607/48; 607/117

(58) Field of Classification Search
    USPC ............................. 607/7, 28, 46, 48, 117, 118
    See application file for complete search history.

(56) References Cited

U.S. PATENT DOCUMENTS

| | | |
|---|---|---|
| 4,977,895 A | 12/1990 | Tannenbaum |
| 5,111,813 A | 5/1992 | Charbonnier et al. |
| 5,342,404 A | 8/1994 | Alt et al. |
| 5,628,317 A | 5/1997 | Starkebaum et al. |
| 5,716,377 A | 2/1998 | Rise et al. |
| 5,836,983 A | 11/1998 | Weijand et al. |
| 5,941,906 A | 8/1999 | Barreras, Sr. et al. |
| 6,029,090 A | 2/2000 | Herbst |
| 6,032,674 A | 3/2000 | Eggers et al. |

(Continued)

FOREIGN PATENT DOCUMENTS

| | | |
|---|---|---|
| WO | WO 2004/075982 | 9/2004 |
| WO | WO 2005/065536 | 7/2005 |
| WO | WO 2005/102449 | 11/2005 |

OTHER PUBLICATIONS

Office action for U.S. Appl. No. 13/403,288, mailed Oct. 16, 2012, 9 pages.

(Continued)

*Primary Examiner* — Tammie K Heller
(74) *Attorney, Agent, or Firm* — Shumaker & Sieffert, P.A.

(57) ABSTRACT

Techniques for adjusting stimulation are disclosed. A medical device measures an impedance associated with one or more electrodes, e.g., the impedance presented to the medical device by a total electrical circuit that includes the one or more electrodes, the conductors associated with the electrodes, and tissue proximate to the electrodes. The medical device stores at least one patient-specific relationship between impedance and a stimulation parameter, and adjusts the value of the stimulation parameter based on the measured impedance according to the relationship. The medical device may store multiple relationships, and select one the relationships based on, for example, an activity level of the patient, posture of the patient, or a current stimulation program or electrode combination used to deliver stimulation. By adjusting a stimulation parameter, such as amplitude, according to such a relationship, the stimulation intensity as perceived by the patient may be kept substantially constant.

19 Claims, 5 Drawing Sheets

(56) References Cited

U.S. PATENT DOCUMENTS

| | | | |
|---|---|---|---|
| 6,319,241 B1 | 11/2001 | King et al. | |
| 6,339,724 B1 | 1/2002 | Thong | |
| 6,684,106 B2 | 1/2004 | Herbst | |
| 6,752,765 B1 | 6/2004 | Strobel et al. | |
| 6,795,737 B2 | 9/2004 | Gielen et al. | |
| 6,978,178 B2 * | 12/2005 | Sommer et al. | 607/28 |
| 6,993,384 B2 | 1/2006 | Bradley et al. | |
| 7,031,773 B1 * | 4/2006 | Levine et al. | 607/28 |
| 7,139,608 B2 | 11/2006 | Ideker et al. | |
| 7,406,351 B2 | 7/2008 | Wesselink | |
| 8,155,753 B2 | 4/2012 | Wesselink | |
| 8,457,759 B2 | 6/2013 | Parker et al. | |
| 2001/0053885 A1 | 12/2001 | Gielen et al. | |
| 2002/0107553 A1 | 8/2002 | Hill et al. | |
| 2002/0123773 A1 | 9/2002 | Molin | |
| 2003/0040776 A1 | 2/2003 | Kroll et al. | |
| 2003/0120323 A1 | 6/2003 | Meadows et al. | |
| 2003/0153959 A1 | 8/2003 | Thacker et al. | |
| 2003/0176807 A1 | 9/2003 | Goetz et al. | |
| 2003/0181960 A1 | 9/2003 | Carter et al. | |
| 2003/0199929 A1 | 10/2003 | Snyder et al. | |
| 2003/0199938 A1 | 10/2003 | Smits et al. | |
| 2004/0015205 A1 | 1/2004 | Whitehurst et al. | |
| 2004/0024421 A1 | 2/2004 | Ideker et al. | |
| 2004/0044377 A1 | 3/2004 | Larsson | |
| 2004/0078058 A1 | 4/2004 | Holmstrom et al. | |
| 2004/0111124 A1 | 6/2004 | Walker | |
| 2004/0111130 A1 | 6/2004 | Hrdlicka et al. | |
| 2004/0116784 A1 | 6/2004 | Gavish | |
| 2004/0116978 A1 | 6/2004 | Bradley | |
| 2004/0138516 A1 | 7/2004 | Osorio et al. | |
| 2004/0147983 A1 | 7/2004 | Czygan | |
| 2004/0158119 A1 | 8/2004 | Osorio et al. | |
| 2004/0220637 A1 | 11/2004 | Zdeblick et al. | |
| 2004/0243192 A1 | 12/2004 | Hepp et al. | |
| 2004/0254483 A1 | 12/2004 | Zdeblick et al. | |
| 2005/0049646 A1 | 3/2005 | Czygan et al. | |
| 2005/0081847 A1 | 4/2005 | Lee et al. | |
| 2005/0119703 A1 | 6/2005 | DiLorenzo | |
| 2005/0216062 A1 | 9/2005 | Herbst | |
| 2005/0222626 A1 | 10/2005 | DiLorenzo | |
| 2005/0240242 A1 | 10/2005 | DiLorenzo | |
| 2006/0004424 A1 | 1/2006 | Loeb et al. | |
| 2006/0009816 A1 | 1/2006 | Fang et al. | |
| 2006/0036186 A1 | 2/2006 | Goetz et al. | |
| 2006/0259079 A1 | 11/2006 | King | |
| 2007/0055315 A1 | 3/2007 | Ideker et al. | |
| 2007/0156206 A1 | 7/2007 | Wahlstrand et al. | |
| 2008/0281379 A1 | 11/2008 | Wesselink | |
| 2008/0288031 A1 | 11/2008 | Wesselink | |

OTHER PUBLICATIONS

Response to Office Action dated Oct. 16, 2012, from U.S. Appl. No. 13/403,288, filed Jan. 4, 2013, 11 pages.
Notification of Transmittal of the International Search Report and the Written Opinion dated Sep. 5, 2006 for application No. PCT/US2006/016220, filed Apr. 28, 2006 (12 pages).
Notification of Transmittal of the International Preliminary Report on Patentability dated Apr. 12, 2007 for application No. PCT/US2006/016323, filed Apr. 28, 2006 (7 pages).
Notification of Transmittal of the International Preliminary Report on Patentability dated Jun. 19, 2007 for application No. PCT/US2006/016220, filed Apr. 2006 (10 pages).
Notification of Transmittal of the International Search Report and the Written Opinion for corresponding patent application no. PCT/US2006/016323, mailed Sep. 4, 2006, (12 pages).
U.S. Patent Application entitled "Impedance-Based Stimulation Adjustment," U.S. Appl. No. 11/414,534, filed Apr. 28, 2006.
Office Action for U.S. Appl. No. 11/414,534, mailed Dec. 17, 2008, 12 pages.
Response to Office Action for U.S. Appl. No. 11/414,534, filed Mar. 17, 2009, 16 pages.
Office Action for U.S. Appl. No. 11/414,534, mailed Jun. 18, 2009, 9 pages.
Response to Office Action for U.S. Appl. No. 11/414,534, filed Sep. 18, 2009, 6 pages.
Final Office Action for U.S. Appl. No. 11/414,534, mailed Dec. 9, 2009, 9 pages.
Response to Final Office Action for U.S. Appl. No. 11/414,534, filed Feb. 3, 2010, 10 pages.
Final Office Action for U.S. Appl. No. 11/414,530, mailed Oct. 20, 2009, 9 pages.
Responsive Amendment to Final Office Action for U.S. Appl. No. 11/414,530, filed Dec. 29, 2009, 13 pages.
Office Action Action for U.S. Appl. No. 11/414,530, mailed Apr. 29, 2009, 8 pages.
Response to Office Action for U.S. Appl. No. 11/414,530, filed Jul. 23, 2009, 7 pages.
Office Action for U.S. Appl. No. 12/181,013, mailed Aug. 23, 2010, 10 pages.
Office Action for U.S. Appl. No. 12/181,047, mailed Aug. 20, 2010, 8 pages.
Request for Continued Examination (RCE) Transmittal and Amendment for U.S. Appl. No. 11/414,534, filed Mar. 9, 2010, 15 pages.
Supplemental Amendment for U.S. Appl. No. 11/414,534, filed Sep. 7, 2010, 7 pages.
Response to Office Action for U.S. Appl. No. 12/181,013, filed Nov. 15, 2010, 8 pages.
Response to Office Action for U.S. Appl. No. 12/181,047, filed Nov. 15, 2010, 11 pages.
Office Action from U.S. Appl. No. 11/414,534, dated Dec. 16, 2010, 12 pages.
Final office action for U.S. Appl. No. 12/181,013, mailed Jan. 6, 2011, 8 pages.
Response to final office action for U.S. Appl. No. 12/181,013, filed Mar. 3, 2011, 8 pages.
Final office action for U.S. Appl. No. 12/181,047, mailed Jan. 7, 2011, 8 pages.
Response to final office action for U.S. Appl. No. 12/181,047, filed Mar. 3, 2011, 10 pages.
Response to office action for U.S. Appl. No. 11/414,534, filed Mar. 10, 2011, 14 pages.
Office Action from U.S. Appl. No. 12/181,013, dated Apr. 22, 2011, 6 pages.
Response to Office Action dated Apr. 22, 2011, from U.S. Appl. No. 12/181,013, filed Jul. 18, 2011, 6 pages.
Office Action from U.S. Appl. No. 12/181,047, dated Apr. 22, 2011, 7 pages.
Response to Office Action dated Apr. 22, 2011, from U.S. Appl. No. 12/181,047, filed Jul. 18, 2011, 9 pages.
Office Action from U.S. Appl. No. 11/414,534, dated May 24, 2011, 12 pages.
Response to Office Action for U.S. Appl. No. 11/414,534, filed Sep. 6, 2011, 12 pages.
Office Action from U.S. Appl. No. 12/717,484, filed Sep. 6, 2011, 12 pages.
Response to Office Action for U.S. Appl. No. 12/717,484, filed Jan. 4, 2011, 15 pages.
Final Office Action from U.S. Appl. No. 12/717,484, dated Apr. 5, 2011, 16 pages.
Response to Final Office Action for U.S. Appl. No. 12/717,484, filed Jun. 16, 2011, 10 pages.
Final Office Action from U.S. Appl. No. 12/181,047, dated Sep. 22, 2011, 8 pages.
Response to Final Office Action for U.S. Appl. No. 12/181,047, filed Nov. 15, 2011, 7 pages.
Final Office Action from U.S. Appl. No. 12/181,013, dated Sep. 14, 2011, 6 pages.
Response to Final Office Action from U.S. Appl. No. 12/181,013, filed Nov. 15, 2011, 3 pages.

* cited by examiner

IMPEDANCE-BASED STIMULATION ADJUSTMENT

This application is a continuation of U.S. application Ser. No. 11/414,534, filed Apr. 28, 2006, and issued as U.S. Pat. No. 8,108,049, on Jan. 31, 2012, which claimed the benefit of U.S. provisional application No. 60/676,609, filed Apr. 30, 2005, the entire contents of both of which are incorporated herein by reference.

TECHNICAL FIELD

The invention is directed to medical devices and, more particularly, medical devices that deliver electrical stimulation.

BACKGROUND

Medical devices deliver electrical stimulation in order treat a variety of ailments or symptoms of patients, such as pain, epilepsy, movement disorders, incontinence, sexual dysfunction, gastroparesis, or other neurological, urological or gastric disorders. The medical devices used to treat such ailments or symptoms may be implantable. Further, whether implanted or not, the medical devices often deliver electrical stimulation to targeted tissue via one or more electrodes carried by one or more leads, which include internal conductors to couple the electrodes to the medical device.

For example, spinal cord stimulation (SCS) has been used to treat chronic pain, such as chronic neuropathic pain of the trunk and limbs. Usually, after a percutaneous trial with an external medical device has shown that SCS is efficacious, an implantable medical device is implanted surgically. The external trial device and the implantable medical device both generate electrical pulses, which may be delivered within the spinal canal by selected electrodes from among a plurality of electrodes. The electrodes are carried by one or more implanted multi-electrode leads, which include conductors to couple the electrodes to the devices. Lead extensions with corresponding conductors may be used to couple the leads and lead conductors to the devices. The trial and implantable medical devices may be coupled to the same leads and extensions, or to different leads or extensions.

For SCS, the one or more multi-electrode leads are typically implanted outside of the dura, in the epidural space. When a lead is implanted in the epidural space, the electrodes carried by the lead are usually approximately two to six millimeters away from the targeted neurons of the spinal cord. Between the electrodes and the neurons to be excited are the dura, the arachnoid membrane, and a layer of cerebrospinal fluid. These elements tend to diffuse electrical currents.

At least in part due to the distance and above-identified elements between the epidurally-located electrodes and target neurons, it is difficult to keep the effect of stimulation constant when there is movement of the implanted electrodes relative to the target neurons. For example, by bending forward, a patient can cause epidurally-implanted electrodes to move several centimeters relative to a target spinal cord level or nerve root. Additionally, when a patient goes from a supine lying position, to sitting, to standing, the space between the epidurally-implanted electrodes and the surface of the dorsal columns of the spinal cord can change significantly. Such movement may require adjustment of stimulation parameters, such as amplitude or pulse width, by a factor of two or more to maintain substantially constant stimulation efficacy.

If the targeted tissue is within the cervical levels of the spinal cord, the movement of the implanted electrodes relative to the targeted tissue may be even more significant, e.g., when the neck is turned or tilted. Some patients experience the stimulation as varying within a range from very painful to no sensation at all with relatively minor movements of the head and neck. The difficulty in maintaining substantially constant stimulation efficacy throughout a range of patient motion has limited usage of SCS therapy, particularly in patients with pain in the upper limbs, shoulders or neck.

SUMMARY

In general, the invention is directed to a medical device that delivers stimulation to a patient via electrodes, measures impedances associated with the electrodes, and adjusts one or more parameters of the stimulation, such as amplitude, based on the measured impedances. The medical device adjusts a stimulation parameter as indicated by a predetermined "patient-specific" relationship between the stimulation parameter and impedance. The relationship is patient-specific in the sense that it is tailored to the particular patient. In this manner, the medical device may adjust the stimulation parameter such that the intensity of the stimulation as perceived by the patient remains substantially constant.

The impedance presented to the medical device is determined by the impedances associated with the electrodes used to deliver stimulation, the conductors associated with the electrodes within one or more leads that carry the electrodes, and tissue proximate to the electrodes. Variation in the presented impedance may occur due to a variety of factors, including degradation or failure of lead materials, changes in patient hydration, and changes in the make up of the tissue proximate to the electrodes. The make up of the tissue proximate to the electrodes may change as the electrodes move relative to the tissue intended to be stimulated. Accordingly, changes in impedance may be due, in part, to movement of the electrodes relative to the tissue intended to be stimulated. The electrodes may move relative to the targeted tissue when the patient is active or assumes a different posture.

The intensity of stimulation as perceived by a patient also varies based on the movement of the electrodes relative to the targeted tissue, e.g., based on the activity or posture assumed by the patient. Consequently, the impedance presented to a medical device may be indicative of intensity of stimulation perceived by a patient. In general, the voltage or current sources within a medical device that output electrical stimulation hold their stimulation at a constant voltage or current amplitude, respectively. Due to changes in the presented impedance over time, the current output by a constant voltage device, and the voltage output by a constant current device, will vary.

However, changes in perceived stimulation intensity may be more closely correlated to changes in the distance between electrodes and target tissue than the changing stimulation output. Consequently, adjustment of stimulation based on a single linear relationship for all patients, derived from Ohm's Law, may not result in consistent perceived stimulation intensity. For example, for some patients, stimulation intensity may be high when impedance is high, contrary to what would be indicated by such a relationship.

According to the invention, at least one patient-specific relationship between impedance and a stimulation parameter, such as amplitude, is determined for the patient. During a relationship-determination period, impedances are measured, and feedback from the patient indicating perceived stimulation intensities is recorded. A relationship between the stimulation parameter and impedance is derived for the patient based on the measured impedances and the feedback.

For example, at impedance values where the patient experiences high stimulation intensity during a trial, a relationship between amplitude and impedance may call for a delivery of stimulation at a lower amplitude. A number of relationships may be developed for the patient, each relationship specific to a stimulation parameter, a posture or activity assumed by a patient, and/or a particular stimulation program and associated combination of electrodes. A programming device may be used to collect measured impedances from a medical device and feedback from the patient, generate the relationships, and provide the relationships to the medical device. In some embodiments, a trial medical device may be used during definition of the relationships, and a permanently implantable medical device may store the relationships for long-term adjustment of stimulation in accordance with the relationships.

A medical device stores the one or more patient-specific relationships, previously determined in the manner discussed above, between a stimulation parameter and impedance. The medical device measures an impedance associated with one or more electrodes, e.g., the impedance presented to the medical device by a total electrical circuit that includes the one or more electrodes, the conductors associated with the electrodes, and tissue proximate to the electrode, and adjusts the stimulation parameter based on the measured impedance according to the impedance/parameter relationships. The medical device may store multiple impedance/parameter relationships, and select one or more of the relationships based on an activity level of the patient, posture of the patient, or the stimulation program or electrode combination currently being used by the medical device to deliver stimulation to the patient.

In one embodiment, the disclosure provides a system comprising stimulation circuitry that delivers stimulation to a patient via electrodes, a memory that stores a predetermined patient-specific relationship between a parameter of the stimulation and impedance, impedance measurement circuitry that measures an impedance associated with the electrodes, and a processor that adjusts the stimulation parameter based on the measured impedance according to the predetermined patient-specific relationship, and controls the stimulation circuitry to deliver the stimulation to the patient via the electrodes according to the adjusted parameter In another embodiment, the disclosure provides a method comprising measuring an impedance associated with electrodes that deliver stimulation to a patient, and adjusting a parameter of the stimulation based on the measured impedance according to a predetermined patient-specific relationship between the parameter and impedance.

In another embodiment, the disclosure provides a system comprising means for delivering stimulation to a patient, means for measuring an impedance during the delivery of the stimulation, and means for adjusting a parameter of the stimulation based on the measured impedance according to a predetermined patient-specific relationship between the parameter and impedance.

In another embodiment, the disclosure provides a system comprising stimulation circuitry that delivers stimulation to a patient via electrodes, impedance measurement circuitry that periodically measures an impedance associated with the electrodes, a user interface, and a processor that receives feedback regarding a perceived intensity of the stimulation via the user interface, and determines a patient-specific relationship between a stimulation parameter and impedance based on the measured impedances and the feedback.

In another embodiment, the disclosure provides a method comprising delivering stimulation to a patient via electrodes, periodically measuring an impedance associated with the electrodes, receiving feedback regarding a perceived intensity of the stimulation from a user, and determining a patient-specific relationship between a stimulation parameter and impedance based on the measured impedances and the feedback.

In another embodiment, the disclosure provides a computer-readable medium comprising instructions. The instructions cause a programmable processor to control delivery of stimulation to a patient via electrodes, receive impedance measurements associated with the electrodes, receive feedback regarding a perceived intensity of the stimulation from a user; and determine a patient-specific relationship between a stimulation parameter and impedance based on the measured impedances and the feedback.

In another embodiment, the disclosure provides a system comprising means for delivering stimulation to a patient via electrodes, means for periodically measuring an impedance associated with the electrodes, means for receiving feedback regarding a perceived intensity of the stimulation from a user, and means for determining a patient-specific relationship between a stimulation parameter and impedance based on the measured impedances and the feedback.

Embodiments of the invention may be capable of providing advantages. For example, by adjusting stimulation according to a relationship between a stimulation parameter and impedance, a medical device may deliver stimulation such that the perceived intensity of the stimulation is substantially constant. Further, because the relationship is patient-specific, the medical device may be able to provide stimulation via electrodes such that the intensity is perceived as being substantially constant despite movement of the electrodes relative to target tissue. As discussed above, movement of electrodes relative to target tissue may result in changes in both the impedance associated with the electrodes and perceived stimulation intensity. However, due to movement of electrodes relative to target tissue, the relationship between impedance and perceived stimulation intensity may be counter-intuitive and, in any event, may vary from patient to patient.

By selecting from multiple relationships based on posture, activity, and/or stimulation program, a medical device may be able to provide stimulation with substantially constant perceived intensity over a wide range of activities and postures, and for each of a variety of stimulation programs, e.g., combinations of electrodes on more or more multielectrode leads, that may be selected by a patient. Additionally, although the techniques of the invention may provide advantages such as substantially constant perceived stimulation intensity when employed to adjust any type of stimulation, including spinal cord stimulation, the invention may be particular advantageous when employed to adjust stimulation delivered to the cervical levels of the spinal cord. As discussed above, patients receiving stimulation at cervical levels of the spinal cord may experience the most significant variations in perceived stimulation intensity when the electrodes move relative to target tissue, e.g., due to the patient moving his or her head or neck.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
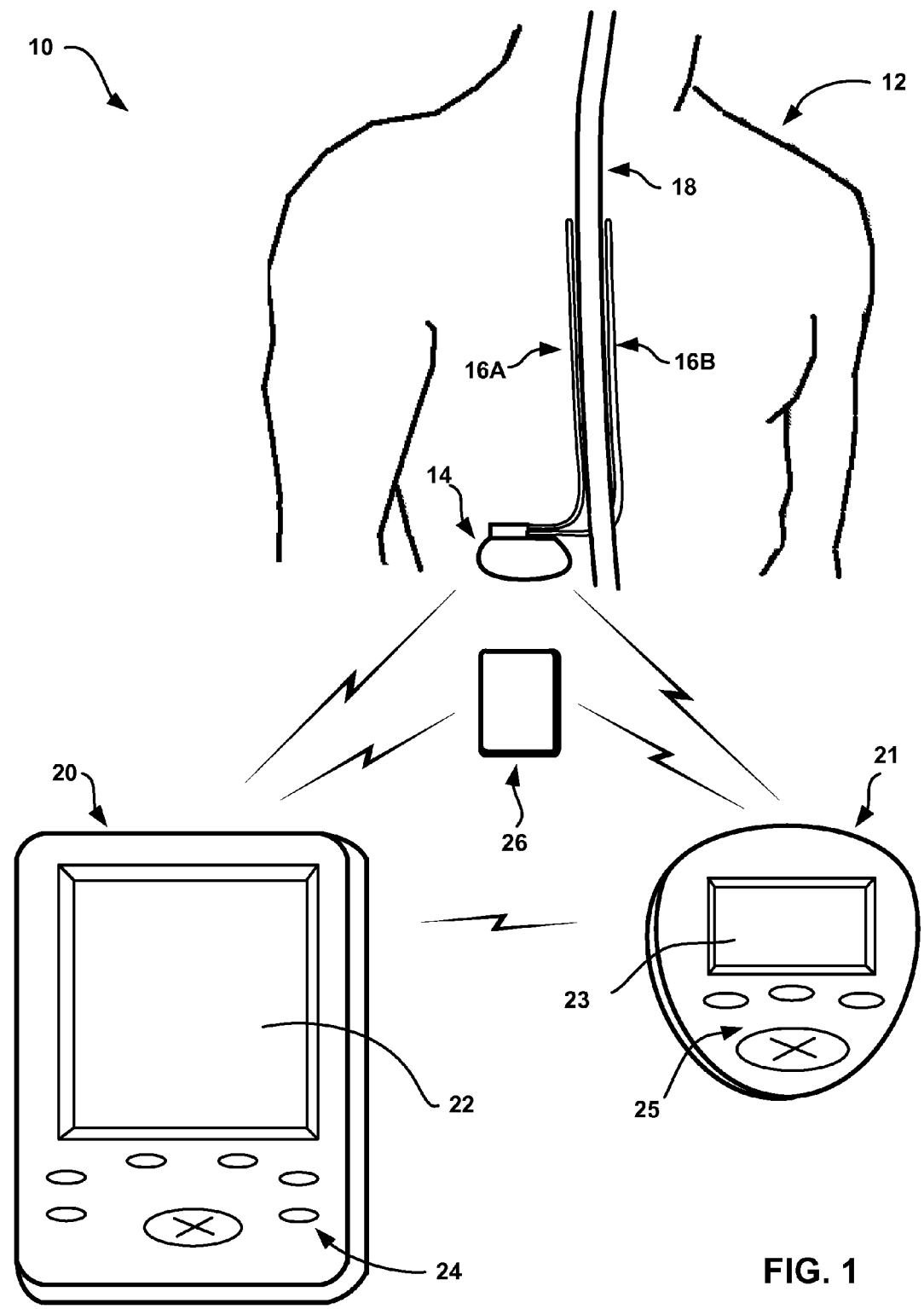
FIG. 1 is a conceptual diagram illustrating an example system including an implantable medical device that adjusts a stimulation parameter based on measured impedance according to a predetermined patient-specific relationship between impedance and the parameter.

FIG. 1 is a conceptual diagram illustrating an example system 10 that includes an implantable medical device (IMD) 14. As will be described in greater detail below, IMD 14 adjusts a stimulation parameter, such as voltage or current amplitude, based on measured impedance. IMD 14 adjusts the stimulation parameter according to a predetermined patient-specific relationship between impedance and the parameter. In this manner, IMD 14 may adjust the stimulation such that the intensity of the stimulation as perceived by patient 12 remains substantially constant despite movement of electrodes used to deliver the stimulation relative to tissues of the patient.

In the example of FIG. 1, IMD 14 delivers stimulation to patient 12 via leads 16A and 16B (collectively "leads 16"). Leads 16 may, as shown in FIG. 1, be implanted proximate to the spinal cord 18 of patient 12, e.g., within the epidural space, and IMD 14 may deliver spinal cord stimulation (SCS) therapy to patient 12 in order to, for example, reduce pain experienced by patient 12. However, the invention is not limited to the configuration of leads 16 shown in FIG. 1, the delivery of SCS therapy, or the delivery of neurostimulation therapy.

For example, leads 16 may be implanted proximate to the thoracic vertebrae, as shown, or alternatively may be implanted proximate to the lumbar or cervical vertebrae. For example, one or more leads 16 may extend from IMD 14 to the brain (not shown) of patient 12, and IMD 14 may deliver deep brain stimulation (DBS) therapy to patient 12 to, for example, treat tremor, Parkinson's disease, epilepsy, or psychological disorders. As further examples, one or more leads 16 may be implanted proximate to the pelvic nerves (not shown) or stomach (not shown), and IMD 14 may deliver stimulation therapy to treat sexual dysfunction, urinary or fecal incontinence, gastroparesis, or obesity. Leads 16 may include lead extensions, as needed, and the implantation location of IMD 14 is also merely exemplary.

As shown in FIG. 1, system 10 also includes a programming device 20. A clinician, for example, may use programming device 20 to program therapy for patient 12, e.g., specify a number of parameters of the stimulation delivered by IMD 14. In embodiments in which IMD 14 delivers stimulation in the form of electrical pulses, such stimulation parameters may include current or voltage pulse amplitude, pulse rate, and pulse width. The stimulation parameters for a program may also include information identifying an "electrode combination," which is a selected subset of one or more electrodes located on one or more multi-electrode leads, e.g., leads 16. The electrode combination also refers to the polarities of the electrodes in the selected subset. The clinician may use programming device 20 to create a number of programs, each program including respective values for such parameters. Further, as will be described in greater detail below, a clinician may use programming device 20 to create or modify one or more patient-specific relationships between impedance and a stimulation parameter, such as amplitude, used by IMD 14 to control delivery of stimulation to patient 12.

Programming device 20 may, as shown in FIG. 1, be a handheld computing device. Programming device 20 includes a display 22, such as a LCD or LED display, to display information to a user. Programming device 20 may also include a keypad 24, which may be used by a user to interact with the programming device. In some embodiments, display 22 may be a touch screen display, and a user may interact with programming device 20 via display 22. A user may also interact with programming device 20 using peripheral pointing devices, such as a stylus or mouse. Keypad 24 may take the form of an alphanumeric keypad or a reduced set of keys associated with particular functions.

System 10 also includes a programming device 21, which may, as shown in FIG. 1, be a handheld computing device. Programming device 21 may also include a display 23 and a keypad 25, to allow patient 12 to interact with programming device 21. In some embodiments, display 23 may be a touch screen display, and patient 12 may interact with programming device 21 via display 23. Patient 12 may also interact with programming device 21 using peripheral pointing devices, such as a stylus or mouse.

Patient 12 may use programming device 21 to control the delivery of neurostimulation therapy by IMD 14. For example, patient 12 may use programming device 21 to select therapy programs defined by the clinician using programming device 20, and also to adjust stimulation parameters within limits set by a clinician. Programming device 21 may store stimulation programs, and provide selected programs to IMD 14 for delivery of stimulation, or IMD 14 may store programs, and programming device 21 may provide an indication of the selected program to IMD 14.

Programming devices 20, 21 are not limited to the handheld computer embodiments illustrated in FIG. 1. Programming devices 20, 21 according to the invention may be any type of computing device. For example, programming devices 20, 21 according to the invention may be a tablet-based computing device, a desktop computing device, or a workstation.

As illustrated in FIG. 1, system 10 may in some embodiments also include a trial stimulator 26. Trial stimulator 26 is an external device that delivers stimulation to patient 12 in a substantially similar manner to IMD 14. Trial stimulator 26 may be used prior to implantation of IMD 14 to determine whether delivery of stimulation by IMD 14 will be efficacious, e.g., relieve symptoms of patient 12. Trial stimulator 26 may be coupled to the same leads 16 as IMD 14 will later be coupled to, or to different leads which will eventually be replaced by leads 16, for delivery of stimulation, e.g., via percutaneous extensions. Trial stimulator 26 may include a user interface to allow a clinician or patient 12 to program and/or control delivery of stimulation to the patient. Additionally or alternatively, the clinician and patient 12 may use programmers 20, 21 to program and/or control delivery of stimulation to the patient by trial stimulator 26.

IMD 14, trial stimulator 26, and programming devices 20, 21 may, as shown in FIG. 1, communicate via wireless communication. Programming devices 20, 21 may, for example, communicate via wireless communication with IMD 14, and in some embodiments trial stimulator 26, using RF telemetry techniques known in the art. Programming devices 20, 21 may communicate with each other, and in some embodiments trial stimulator 26, using any of a variety of local wireless communication techniques, such as RF communication according to the 802.11 or Bluetooth specification sets, infrared communication according to the IRDA specification set, or other standard or proprietary telemetry protocols.

Programming devices 20, 21 and trial stimulator 26 need not communicate wirelessly, however. For example, programming devices 20, 21 and trial stimulator 26 may communicate via a wired connection, such as via a serial communication cable, or via exchange of removable media, such as magnetic or optical disks, or memory cards or sticks. Further, programming device 20 may communicate with one or more of IMD 14, trial stimulator 26, and programming device 21 via remote telemetry techniques known in the art, communicating via a local area network (LAN), wide area network (WAN), public switched telephone network (PSTN), or cellular telephone network, for example.

Figure 2:
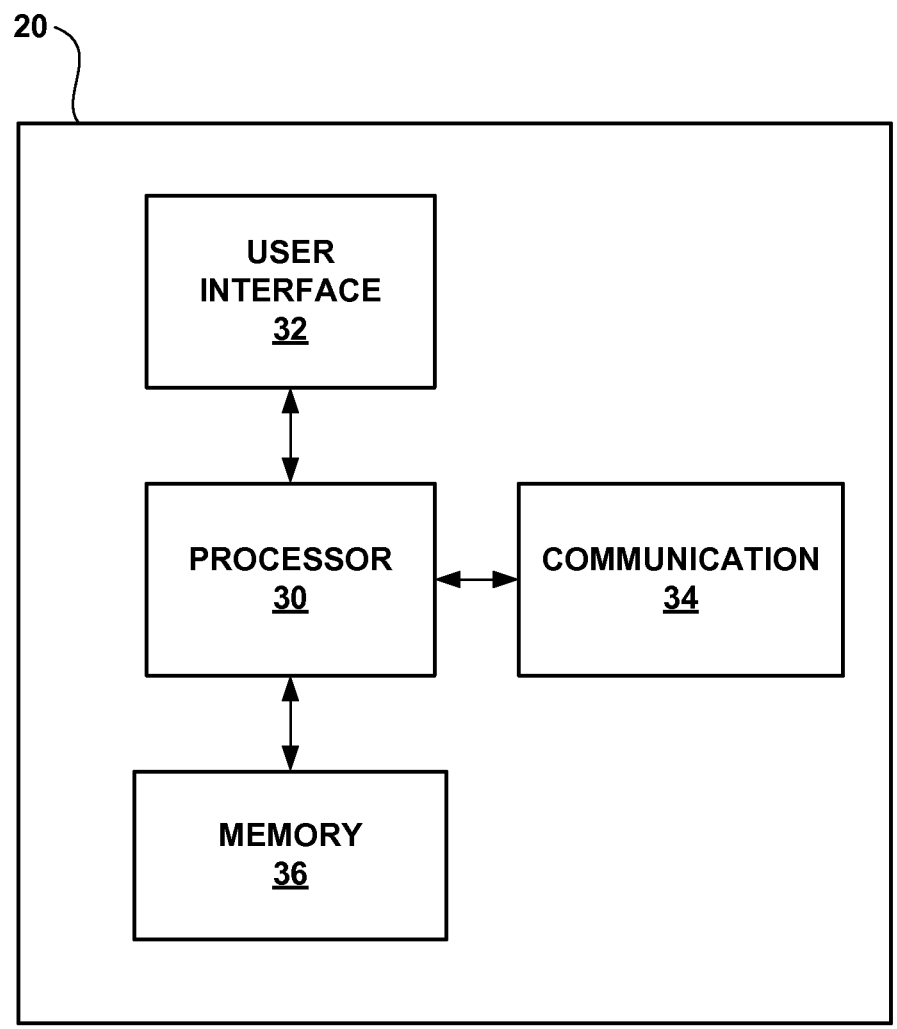
FIG. 2 is functional block diagram illustrating a programming device.

FIG. 2 is functional block diagram further illustrating programming device 20. A clinician may interact with a processor 30 via a user interface 32 in order to create stimulation programs for patient 12. Processor 30 may provide stimulation programs created in this manner to IMD 14 and, in some embodiments, trial stimulator 26. Additionally, the clinician and/or patient 12 may interact with processor 30 to create one or more patient-specific relationships between impedance and a stimulation parameter, e.g., pulse amplitude, pulse width, pulse rate, or electrode combinations, for patient 12. Processor 30 provides the relationships to IMD 14, which uses the relationships to adjust one or more stimulation parameters based on measured impedances.

More particularly, IMD 14 or trial stimulator 26 delivers stimulation to patient 12 during a "relationship-definition" period. The IMD or trial stimulator measures impedances during the relationship definition period, and processor 30 receives the measured impedances from the IMD or trial stimulator. Processor 30 also receives feedback relating to the intensity of the stimulation delivered by the IMD or trial stimulator, as perceived by patient 12, from the patient and/or clinician, via user interface 32. Processor 30 determines a relationship between a stimulation parameter and impedance based on the measured impedances and the feedback, and provides the relationship to IMD 14. Processor 30 may determine respective relationships for each of a plurality of stimulation parameters based on the feedback and measured impedances.

Further, in some embodiments, IMD 14 or trial stimulator 26 delivers stimulation according to a plurality of electrode combinations, e.g., programs, and/or patient 12 assumes a plurality of postures or activity levels, during the relationship-definition period. In such embodiments, processor 30 may associate measured impedances and received feedback with the programs, postures or activity levels occurring when measured or received. Further, in such embodiments, processor 30 may determine one or more respective patient-specific relationships between a stimulation parameter and impedance for each of the electrode combinations, postures, or activity levels based on the impedances and feedback associated with the electrode combinations, postures, or activity levels.

Processor 30 communicates with IMD 14 through communication circuitry 34, which may include circuitry for RF or inductive wireless telemetry, as is known in the art. Communication circuitry 34 may also include circuitry for other wireless, wired and or networked communication, as discussed above with reference to FIG. 1. User interface 32 may include display 22 and keypad 24, and may also include a touch screen or peripheral pointing devices as described above. Processor 30 may include any one or more of a microprocessor, a controller, a digital signal processor (DSP), an application specific integrated circuit (ASIC), a field-programmable gate array (FPGA), discrete logic circuitry, or the like.

Programming device 20 also includes a memory 36. In addition to stimulation programs and impedance/stimulation parameter relationships created using programming device 20, memory 36 may store program instructions that, when executed by processor 30, cause the processor and programming device 20 to perform the functions ascribed to them herein. Memory 36 may include any volatile, non-volatile, fixed, removable, magnetic, optical, or electrical media, such as a random access memory (RAM), read-only memory (ROM), CD-ROM, hard disk, removable magnetic disk, memory cards or sticks, non-volatile RAM (NVRAM), electronically erasable programmable ROM (EEPROM), flash memory, and the like.

Figure 3:
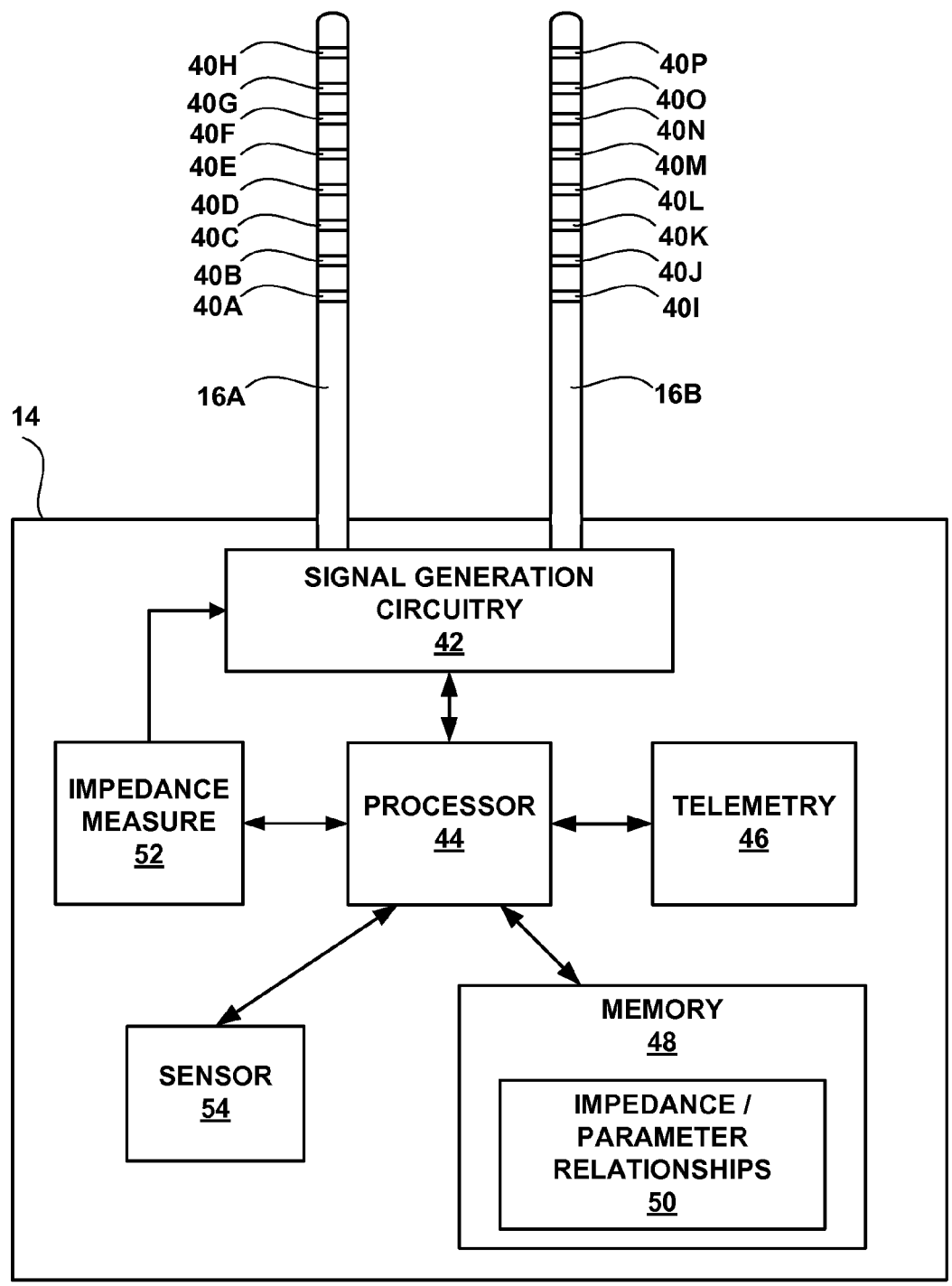
FIG. 3 is a functional block diagram further illustrating the implantable medical device of FIG. 1.
Figure 5:
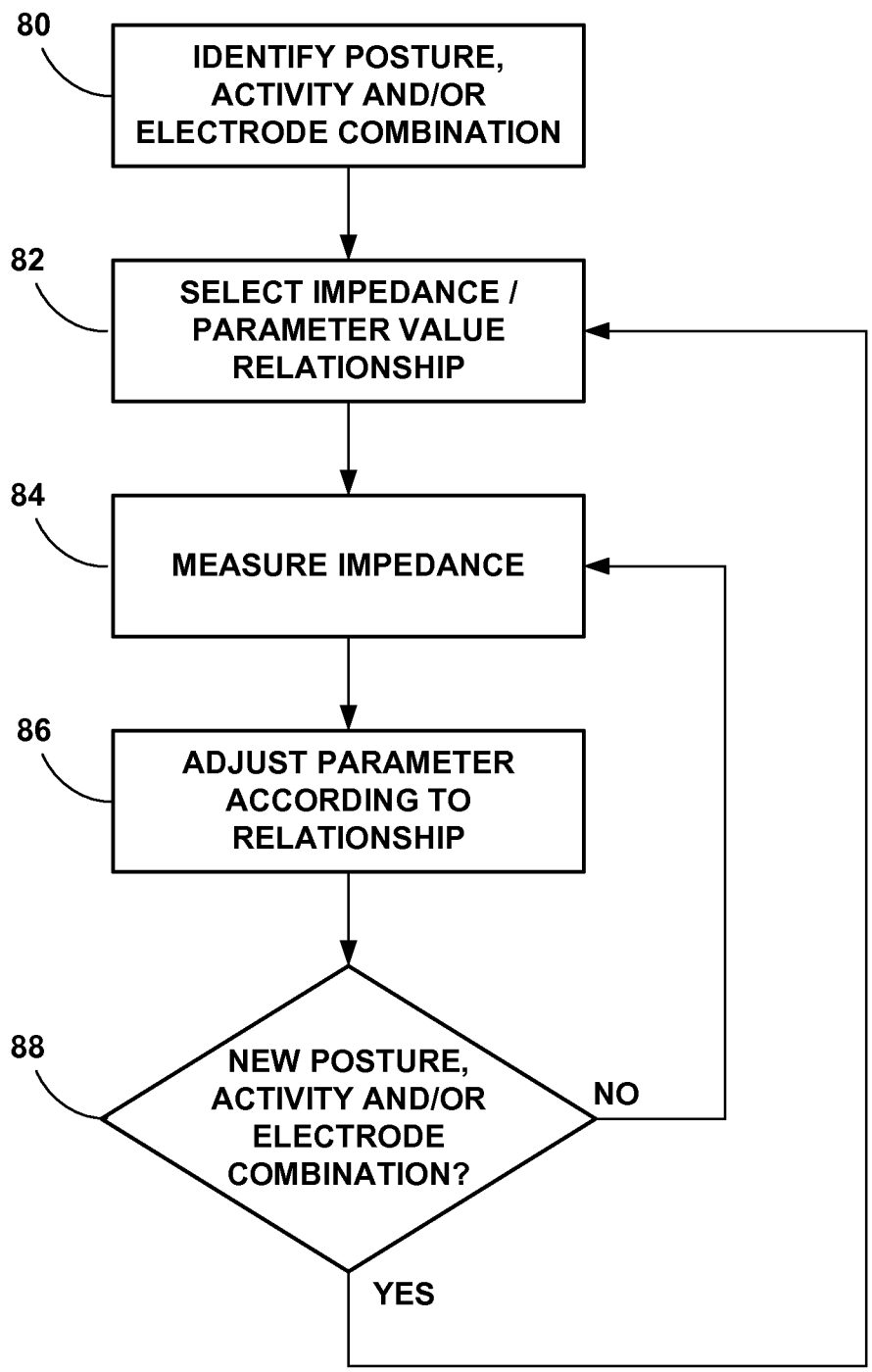
FIG. 5 is a flow diagram illustrating an example method for adjusting stimulation according to at least one patient-specific relationship between a stimulation parameter and impedance.

FIG. 3 is a functional block diagram further illustrating IMD 14 coupled to leads 16. In the illustrated example, lead 16A includes electrodes 40A-H, and lead 16B includes electrodes 40I-P (collectively "electrodes 40"). Electrodes 40 may be ring electrodes. The configuration, type and number of electrodes 40 illustrated in FIG. 5 are exemplary. For example, leads 16A and 16B may each include fewer than eight electrodes 40, and the electrodes 40 need not be arranged linearly on each of leads 16A and 16B. Further, in other embodiments, leads 16 may have other shapes, such as paddle-like shapes with electrodes located on one or more sides of the paddle, or may include complex, multi-dimensional electrode array geometries.

Electrodes 40 are electrically coupled to signal generation circuitry 42 within IMD 14 via respective conductors within leads 16. Under the control of a processor 44, signal generation circuitry 42 generates electrical signals, which in some cases are therapeutic stimulation, for delivery to patient 12 via electrodes 40. In particular, processor 44 controls signal generation circuitry 42 to generate signals with selected values for parameters such as pulse amplitude, width and rate. Processor 44 also controls coupling of electrodes 40 specified by an electrode combination to signal generation circuitry 42, e.g., controls switches that couple the selected electrodes to the signal generation circuitry. Signal generation circuitry 42 may include, for example, one or more output pulse generators, which may deliver constant voltage or current pulses, and switches to couple the pulse generator to electrodes 40 as specified by an electrode combination.

For therapeutic stimulation, processor 44 may receive the values for stimulation parameters, e.g., a voltage or current pulse amplitude, a pulse width, a pulse rate and an electrode combination, from programming device 20 via telemetry circuitry 46. More particularly, processor 44 may receive one or more programs from programming device 20, each program including respective values for such stimulation parameters. Processor 44 may store programs received from programming device 20 in a memory 48.

Processor 44 may control delivery of therapeutic stimulation by signal generation circuitry 42 according to one or more programs most recently received from programming device 20. Alternatively, processor 44 may control delivery of therapeutic stimulation according one or more programs selected from among those stored in memory 48. Processor 44 may select programs from memory 48 automatically, e.g., according to a schedule, or based on user selection as indicated by signals received from one of programming devices 20, 21.

As illustrated in FIG. 3, memory 48 also stores one or more relationships 50 between impedance and a stimulation parameter, such as pulse amplitude, pulse width, pulse rate, or electrode combination. Relationships 50 may be linear or non-linear, and may take the form of look-up tables, equations, or the like. Processor 44 periodically controls impedance measurement circuitry 52 to measure one or more impedances associated with one or more of electrodes 40, and adjusts one or more stimulation parameters based on the impedances and one or more currently selected relationships 50.

For example, if processor 44 is controlling signal generation circuitry 42 to deliver stimulation according to a selected program, processor 44 may control impedance measurement circuitry 52 to measure one or more impedances associated with the combination of electrodes for the selected program. Processor 44 may then adjust a stimulation parameter, such as amplitude, for the program based on the measured impedance and a relationship 50 between amplitude and impedance. Processor 44 may adjust each of a plurality of stimulation parameters according to a respective relationship 50 between the stimulation parameter and impedance. Processor 44 may update the values of the stimulation parameters for the programs stored in memory 48 based on the adjustments. In this manner, IMD 14 may deliver stimulation with an intensity that patient 12 perceives to be substantially constant.

Impedance measurement circuitry 52 may include resistors, capacitors, or other known circuitry for sampling and/or holding a value of one or both of voltage or current when a pulse is delivered by signal generation circuitry. Processor 44 may determine the impedance based on the measured voltage and/or current using any of a variety of known techniques. For example, in some embodiments, signal generation circuitry 42 delivers a voltage pulse with a decay, and measurement circuitry 52 samples and holds the final voltage value of the pulse at the end of the pulse. Based on the initial, e.g., programmed, voltage for the pulse, and the sampled final voltage, processor 44 may determine the impedance associated with a combination of electrodes using known techniques, such as those described in commonly-assigned U.S. Pat. No. 6,978,171, which issued to Goetz et al. on Dec. 20, 2005, and is incorporated herein in its entirety by reference. Equations or the like used by processor 44 to determine the impedance or current may be stored in memory 48.

Processor 44 may periodically control signal generation circuitry 42 to deliver a dedicated, e.g., non-therapeutic, sub-threshold, signal via a pair of electrodes 40, or one of the electrodes and a "can" electrode of IMD 14, and control impedance measurement circuitry 52 to measure the impedance during the delivery. The dedicated signal may be, for example, a pulse having an amplitude or pulse width significantly lower than that of therapeutic stimulation pulses. Because of their low amplitude and/or pulse width, such dedicated pulses may not result in any therapeutic or adverse effects, e.g., may not activate any nerves or other tissues, and may therefore be referred to as sub-threshold pulses in the sense that the are below a threshold sufficient for therapy.

Processor 44 may periodically control signal generation circuitry 42 and impedance measurement circuitry 52 to perform such an impedance measurement for each of any number of electrodes 40. For example, processor 44 may control individual measurements of all of electrodes 40, or only the electrodes in the electrode combinations for the one or more programs currently used for delivery of stimulation. In such embodiments, processor 44 may determine an average, sum, or some other combination or synthesis of the individually measured impedances, and adjust a stimulation parameter based on that value according to one of relationships 50.

In other embodiments, processor 44 may control signal generation circuitry 42 to deliver a single dedicated, e.g., sub-threshold, signal to, for example, all of electrodes 40, or the electrodes in the currently active electrode combinations. In such embodiments, processor 44 may control measurement circuitry 52 to measure the impedance during delivery of the signal. Further, rather than dedicated, sub-threshold measurements, processor 44 may control impedance measurement circuitry 52 to measure the impedance during delivery of therapeutic stimulation to patient 12 by signal generation circuitry 42 via the one or more combinations of electrodes for one or more current programs. In either of these cases, processor may adjust the one or more stimulation parameters based on the measured impedance according to the one or more relationships. In each of the above examples, processor 44 determines an impedance value associated with electrodes 40 used to deliver stimulation to patient 12, and adjusts a stimulation parameter based on the impedance and one of relationships 50 stored in memory 48.

In some embodiments, as will be described in greater detail below, processor 44 may select one or more relationships 50 from among a plurality of relationships 50 stored in memory 48 to be the current relationships for adjustment of one or more stimulation parameters. Processor 44 may select a single relationship 50 to adjust a single stimulation parameter, or a plurality of respective relationships to adjust a plurality of stimulation parameters. Processor 44 may select relationships 50 based on a currently selected stimulation program, e.g., select a relationship associated with the program or electrode combination for the program. Additionally or alternatively, processor 44 may select relationships 50 based on the activity level or posture of patient 12. For example, processor 44 may select a relationship associated with the current activity level or posture of patient 12.

As shown in FIG. 3, IMD 14 may include one or more sensors 54. Although illustrated as located within IMD 14, e.g., within a housing of the IMD, sensors 54 may be coupled to IMD 14 wirelessly or via leads. Sensors 54 may include any sensor that generates a signal that varies as a function of patient activity and/or posture, such as one or more accelerometers, a piezoelectric elements, mercury switches, electromyogram (EMG) electrodes, or electrocardiogram (ECG) electrodes. Sensors 54 may generate a signal that varies as a function of gross muscle movement, footfalls, and/or posture.

A plurality of orthogonally aligned sensors 54, such as accelerometers, mercury switches, gyros, or magnetometers, may generate signals that indicate patient posture. In addition to being oriented orthogonally with respect to each other, each of sensors 54 used to detect the posture of patient 12 may be generally aligned with an axis of the body of patient 12. In exemplary embodiments, IMD 14 includes three orthogonally oriented sensors 54.

When sensors 54 include accelerometers, for example, that are aligned in this manner, processor 44 may monitor the magnitude and polarity of DC components of the signals generated by the accelerometers to determine the orientation of patient 12 relative to the Earth's gravity, e.g., the posture of patient 12, and identify when and how often the posture changes. Further information regarding use of orthogonally aligned accelerometers to determine patient posture may be found in a commonly assigned U.S. Pat. No. 5,593,431, which issued to Todd J. Sheldon, and is incorporated herein by reference in its entirety. An example sensor 54 that may be used to detect patient activity, including posture changes, is an Inertial Sensor: 3Axis—2 g/6 g Linear Accelerometer, commercially available from STMicroelectronics, Inc. of Geneva, Switzerland.

Processor 44 may identify activity levels and postures based on the signals generated by sensors 54 in any of a variety of ways. For example, processor 44 may identify an activity level as a current number of activity counts determined based on an accelerometer or piezoelectric element signal, or an average number of activity counts over a period of time. As another example, processor 44 may identify an activity level as a current or average heart rate value. Further, processor 44 may determine whether such a current or average value is within one of a plurality of predetermined activity level categories or ranges, such as inactive, activities of daily living, or high activity.

Similarly, processor 44 may determine which of a plurality of predefined postures patient 12 is within based on signals generated by a plurality of sensors 54, e.g., a plurality of orthogonally aligned accelerometers. For example, processor 44 may determine whether patient 12 is prone or standing based on such signals. Memory 48 may store a plurality of thresholds or ranges that may be used by processor 44 to determine which activity categories or postures patient 12 is within based on the signals generated by one or more sensors 54.

Processor 44 may include a microprocessor, a controller, a DSP, an ASIC, an FPGA, discrete logic circuitry, or the like. Memory 48 may include any volatile, non-volatile, magnetic or electrical media, such as a RAM, ROM, NVRAM, EEPROM, flash memory, or the like. In some embodiments, in addition to relationships 50 and one or more stimulation programs, memory 48 stores program instructions that, when executed by processor 44, cause IMD 14 and processor 44 to perform the functions attributed to them herein.

Figure 4:
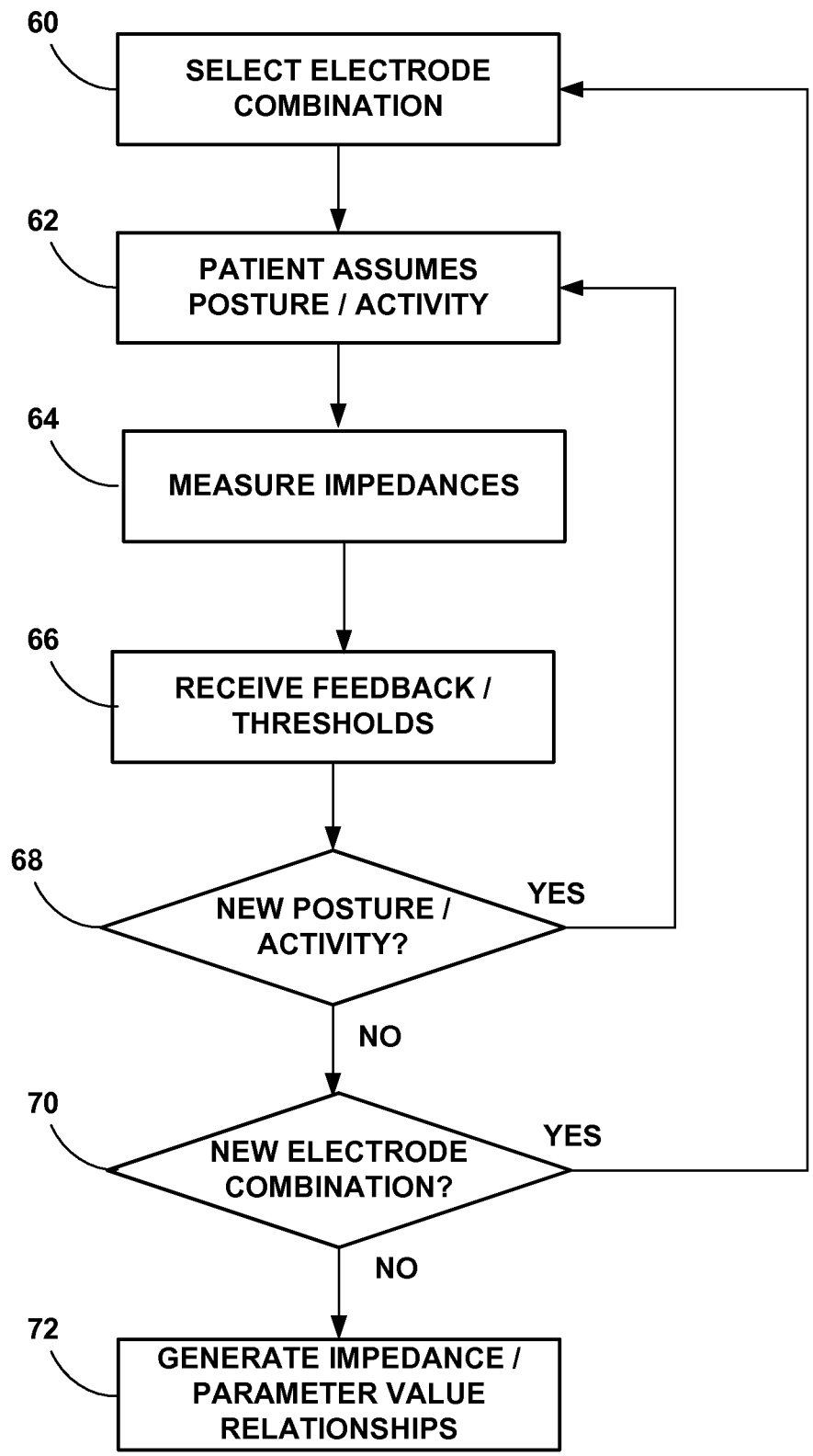
FIG. 4 is a flow diagram illustrating an example method for generating patient-specific relationships between a stimulation parameter and impedance.

FIG. 4 is a flow diagram illustrating an example method for generating one or more patient-specific relationships 50, each of the relationships between a stimulation parameter and impedance, which may be performed by programming device 20 and IMD 14. According to the method, an electrode combination is selected (60), and IMD 14 delivers stimulation via the selected electrode combination. For example, a stimulation program created for the patient that includes a particular electrode combination may be selected, and IMD 14 may deliver stimulation according to the program. IMD 14, programming device 20, or a user using programming device 20, such as a clinician, may select the electrode combination.

During delivery of stimulation via the electrode combination, the patient assumes a posture and/or activity, such as standing, sitting, laying down, walking or running (62), and may move normally within the assumed posture and/or activity. IMD 14, independently or as directed by programming device 20, measures impedances while the patient is within the assumed posture and/or activity (64). Further, programming device 20 receives subjective feedback regarding the intensity of the stimulation as perceived by patient 12 from the patient and/or a clinician while the patient is within the assumed posture and/or activity (66). Such feedback may include numerical ratings of stimulation intensity, pain and/or paresthesia maps, stimulation parameter adjustments, or perception, tolerance or other thresholds determined by varying stimulation amplitude.

Impedance measurement (64) and feedback collection (66) may be repeated for each of plurality of postures/activities assumed by patient 12 during delivery of stimulation by IMD 14 via a single electrode combination, e.g., according to a single program (68, 62). IMD 14 may deliver stimulation via a plurality of electrode combinations (60, 70). Based on the measured impedances and received feedback, programming device 20 may generate a plurality of relationships 50 associated with particular electrode combinations, postures, or activities (72). Alternatively, a plurality of relationships may be associated only with particular postures/activities, or only with particular electrode combinations, or a single relationship for patient 12 may be generated to be used for without respect to electrode combination or posture/activity.

Further, for each electrode combination, posture, and/or activity, programming device 20 may determine a plurality of relationships. Each relationship associates one of a plurality stimulation parameters with impedance. For example, for a particular combination of electrode combination and posture, programming device 20 may determine a first relationship between amplitude and impedance, and a second relationship between pulse width and impedance. The relationships may, for example, associate stimulation parameter values, e.g., amplitudes, with impedance values or ranges. As another example, the relationships may associate absolute or percentage changes in the stimulation parameter value with impedance values or ranges. In other words, a relationship may specify that voltage amplitude should be 4.5 Volts within an impedance range, or that voltage amplitude should decrease by 1.0 Volt or 20 percent when impedance exceeds a threshold value. These examples are merely exemplary, and the invention is not limited to any particular type of relationship between impedance and stimulation parameters.

The example method illustrated in FIG. 4 may be structured. For example, programming device 20 or IMD 14 may regularly select new electrode combinations during a relationship-definition period, e.g., according to a schedule or list of stimulation programs. Further, programming device 20 may prompt patient to assume postures or activities, prompt IMD 14 to measure impedance, and prompt patient 12 to enter feedback coinciding with the impedance measurement. Alternatively, the method may be implemented in a more ad hoc manner in which the patient is free to change electrode combinations, postures and activities, and to enter feedback into programming device 20, as desired. IMD 14 may, for example, regularly identify postures or activities, measure impedances, and associate the impedances with the current postures, activities and/or electrode combinations. Programming device 20 may receive such information from IMD 14, and associate feedback received from the patient or a clinician with contemporaneous postures, activities and/or electrode combinations for determination of one or more relationships between a stimulation parameter and impedance.

FIG. 5 is a flow diagram illustrating an example method for delivering stimulation according to a selected patient-specific relationship 50 between a stimulation parameter, such as amplitude, and impedance. The example method may be performed by IMD 14. IMD 14 may identify a posture, activity or activity level, and/or a current electrode combination (80). IMD 14 may identify the activity or posture based on the signals output by one or more sensors 54, or based on input received from patient 12 via programming device 21. Further, IMD 14 may identify the current electrode configuration from the stimulation program currently used to deliver stimulation to patient 12.

IMD 14 selects an impedance/parameter value relationship 50 based on the posture, activity, electrode combination, or a combination thereof (82). IMD 14 measures an impedance associated with one or more of electrodes 40 (84). For example, IMD 14 may measure the impedance associated with the electrodes of the current electrode combination during delivery of stimulation via the electrode combination. IMD 14 adjusts the parameter value based on the measured impedance and the selected relationship 50 (86). For example, IMD 14 may adjust amplitude by a percentage based on a measured impedance according to a relationship 50 between amplitude and impedance. IMD 14 periodically measures impedances and adjusts the parameter value according to the selected relationship until a new posture, activity or electrode combination is detected (88).

In some embodiments, IMD 14 may adjust a plurality of stimulation parameters based on a measured impedance and respective relationships for each of the stimulation parameters. In other words, each posture, activity, electrode combination, or combination thereof may be associated with a plurality of relationships, each between a respective stimulation parameter and impedance.

Further, in some embodiments, IMD 14 may deliver stimulation according to a plurality of programs at any given time, e.g., in an alternating or interleaved manner. Accordingly, IMD 14 may select one or more relationships 50 for each of the programs, e.g., each of the electrode combinations of the programs, and adjust one or more stimulation parameters for each of the programs based on measured impedances. IMD 14 may measure a common impedance for adjustment of all of the programs, or respective impedances for each of the programs. For example, IMD 14 may measure a respective impedance for each of the programs during delivery of stimulation according to the programs.

Many embodiments of the invention have been described. However, one of ordinary skill in the art will appreciate that various modifications may be made to the described embodiments without departing from the scope of the present invention. For example, although relationship-definition according to the invention has been described as being performed by programming device 20, any one or more of IMD 14, programming devices 20, 21, or some other computing device, may determine relationships 50 in the manner described above. Further, relationship-definition need not be limited to initial programming, and may occur at any time. For example, previously determined relationships 50 may be updated or replaced during a subsequent relationship-definition period, which may involve implementation of the method of FIG. 4.

Additionally, although described in the context of implantable medical devices, any implanted or external device may adjust stimulation parameters according to the invention. Further, the invention is not limited to embodiments in which the stimulation delivering medical device adjusts the stimulation parameter. In some embodiments, a programming device or other computing device stores relationships 50, receives measured impedances from the stimulation delivering medical device, and controls the medical device to adjust stimulation parameters based on the measured impedances and the relationships.

Further, the invention is not limited to embodiments in which IMD 14 is used during relationship definition. In some embodiments, trial stimulator 26 delivers stimulation, measures impedances, and determines activities and/or postures during a relationship-definition period. Trial stimulator 26 may include circuitry, e.g., a processor, signal generation circuitry, impedance measurement circuitry, and sensors, similar to that of IMD 14 as illustrated in FIG. 3. In such embodiments, the developed relationships may be provided to IMD 14, e.g., by programming device 20, when IMD 14 is implanted in patient 12.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure Also, the invention is not limited embodiments in which sensors 54 are used to identify postures, activities, or activity levels. In some embodiments, as described above, patient 12 may indicate what posture, activity, or activity level they are currently assuming, engaged, or within via a programming device, e.g., programming device 21. These and other embodiments are within the scope of the following claims.

The invention claimed is:

1. A system comprising:
   stimulation circuitry that delivers electrical stimulation to a patient via electrodes;
   a memory that stores a predetermined patient-specific relationship between a plurality of electrode combinations and impedance, wherein each electrode combination of the plurality of electrode combinations defines a respective subset of the electrodes and the polarities of the electrodes of the subset;
   impedance measurement circuitry that measures an impedance associated with the electrodes; and
   a processor configured to select an electrode combination from the plurality of electrode combinations according to the predetermined patient-specific relationship based on the measured impedance, and control the stimulation circuitry to deliver the stimulation to the patient via the selected electrode combination, wherein the stimulation circuitry delivers neurostimulation to the patient via the electrodes.

2. The system of claim 1, wherein the predetermined patient-specific relationship between the plurality of electrode combinations and impedance is derived from previously measured values of impedance of the patient.

3. The system of claim 2, wherein the predetermined patient-specific relationship between the plurality of electrode combinations and impedance is further derived from feedback regarding stimulation delivered contemporaneous with the previously measured values of the impedance.

4. The system of claim 3, wherein the feedback indicates the intensity of the stimulation delivered as perceived by the patient.

5. The system of claim 1,
   wherein the memory stores a plurality of predetermined patient-specific relationships between the plurality of electrode combinations and impedance, and
   wherein the processor is configured to select the predetermined patient-specific relationship from among the plurality of predetermined patient-specific relationships.

6. The system of claim 5, wherein the processor is configured to identify at least one of an activity level or a posture of the patient, and select the predetermined patient-specific relationship from among the plurality of predetermined patient-specific relationships based on the activity level or posture.

7. The system of claim 1, wherein the electrodes are implanted proximate to a spinal cord of the patient, and the stimulation circuitry delivers spinal cord stimulation via the electrodes.

8. The system of claim 1, further comprising an implantable medical device, wherein the implantable medical device includes the stimulation circuitry, the memory, the impedance measurement circuitry, and the processor.

9. The system of claim 1, wherein the processor is further configured to detect a change in the measured impedance and select another patient-specific one of the electrode combinations based on the change in the measured impedance according to the predetermined patient-specific relationship.

10. The system of claim 1, wherein the processor is further configured to:
    control the stimulation circuitry to deliver the stimulation to the patient via the selected electrode combination according to a first set of stimulation parameters, the first set of stimulation parameters selected based on the measured impedance,
    detect a change in the measured impedance, and
    select a second set of stimulation parameters based on the changed measured impedance.

11. A method comprising:
    measuring an impedance associated with electrodes that deliver electrical stimulation to a patient;
    selecting an electrode combination from a plurality of electrode combinations according to a predetermined patient-specific relationship between the plurality of electrode combinations and impedance based on the measured impedance, wherein each electrode combination of the plurality of electrode combinations defines a respective subset of the electrodes and the polarities of the electrodes of the subset; and
    controlling delivery of the electrical stimulation to the patient via the selected electrode combination, wherein the electrical stimulation comprises neurostimulation.

12. The method of claim 11, wherein the predetermined patient-specific relationship between the plurality of electrode combinations and impedance is derived from previously measured values of impedance of the patient.

13. The method of claim 12, wherein the predetermined patient-specific relationship between the plurality of electrode combinations and impedance is further derived from feedback regarding stimulation delivered contemporaneous with the previously measured values of the impedance.

14. The method of claim 13, wherein the feedback indicates the intensity of the stimulation delivered as perceived by the patient.

15. The method of claim 11, further comprising selecting the predetermined patient-specific relationship from among a plurality of predetermined patient-specific relationships.

16. The method of claim 15, further comprising identifying at least one of an activity level or a posture of the patient, wherein selecting the predetermined patient-specific relationship comprises selecting the predetermined patient-specific relationship based on the activity level or posture.

17. The method of claim 11, wherein the electrical stimulation comprises spinal cord stimulation.

18. A system comprising:
    means for delivering electrical stimulation to a patient, wherein the electrical stimulation comprises neurostimulation;
    means for measuring an impedance associated with electrodes that deliver the electrical stimulation to a patient;
    means for selecting an electrode combination from a plurality of electrode combinations according to a predetermined patient-specific relationship between the plurality of electrode combinations and impedance based on the measured impedance, wherein each electrode combination of the plurality of electrode combinations defines a respective subset of the electrodes and the polarities of the electrodes of the subset; and
    means for controlling the delivery means to deliver the electrical stimulation to the patient via the selected electrode combination.

19. A non-transitory computer-readable storage medium comprising instructions that cause a programmable processor to:
    selecting an electrode combination from a plurality of electrode combinations according to a predetermined patient-specific relationship between the plurality of electrode combinations and impedance based on the measured impedance, wherein each electrode combination of the plurality of electrode combinations defines a respective subset of the electrodes and the polarities of the electrodes of the subset; and
    control delivery of electrical stimulation to the patient via the selected electrode combination, wherein the electrical stimulation comprises neurostimulation.

* * * * *

UNITED STATES PATENT AND TRADEMARK OFFICE
CERTIFICATE OF CORRECTION

Page 1 of 1

PATENT NO. : 8,825,175 B2
APPLICATION NO. : 13/348943
DATED : September 2, 2014
INVENTOR(S) : Gary King It is certified that error appears in the above-identified patent and that said Letters Patent is hereby corrected as shown below:

In the Claims

Column 16, line 34: "selecting an electrode combination from a" should correctly read -- select an electrode combination from a --.

Signed and Sealed this
Twenty-eighth Day of April, 2015

Michelle K. Lee
*Director of the United States Patent and Trademark Office*